United States Patent [19]

Abrutyn

[11] Patent Number: 4,762,703

[45] Date of Patent: Aug. 9, 1988

[54] NITROCELLULOSE FREE NAIL LACQUER COMPOSITION

[75] Inventor: Eric S. Abrutyn, Middletown, N.Y.

[73] Assignee: Dow Corning Corp., Midland, Mich.

[21] Appl. No.: 87,998

[22] Filed: Aug. 18, 1987

Related U.S. Application Data

[63] Continuation-in-part of Ser. No. 809,846, Dec. 17, 1985, abandoned, which is a continuation of Ser. No. 635,723, Jul. 30, 1984, abandoned, which is a continuation of Ser. No. 342,397, Jan. 25, 1982, abandoned.

[51] Int. Cl.$^4$ ............................................. A61K 7/043
[52] U.S. Cl. ........................................ 424/61; 424/81; 524/555; 526/304
[58] Field of Search ................. 424/61, 81; 526/304; 524/555

[56] References Cited

U.S. PATENT DOCUMENTS

| | | | |
|---|---|---|---|
| 3,277,056 | 10/1966 | Coleman | 526/259 |
| 3,298,113 | 1/1967 | Friedman | 34/219 |
| 3,607,816 | 9/1971 | Frankenthal et al. | 260/31.2 X |
| 3,735,003 | 5/1973 | Zimmer et al. | 424/47 |
| 3,840,490 | 10/1974 | Gadzala et al. | 524/850 |
| 3,864,294 | 2/1975 | Busch | 424/61 X |
| 3,927,199 | 12/1975 | Micchelli et al. | 424/47 |
| 3,927,203 | 12/1975 | Seymar et al. | 424/61 |
| 3,998,997 | 12/1976 | Maudood et al. | 526/271 |
| 4,097,589 | 6/1978 | Shansky | 424/61 |
| 4,128,634 | 12/1978 | Hase et al. | 424/81 |
| 4,129,545 | 12/1978 | Suramori et al. | 524/555 |
| 4,179,304 | 12/1979 | Rossomando | 424/61 X |
| 4,240,450 | 12/1980 | Grollier et al. | 424/61 |
| 4,283,324 | 8/1981 | Duffy | 424/61 X |
| 4,289,752 | 9/1981 | Mahieu et al. | 424/61 |
| 4,321,175 | 3/1983 | Schmidt et al. | 524/555 |
| 4,322,516 | 3/1982 | Wiest et al. | 526/307.7 |
| 4,330,640 | 5/1982 | Buchwalter | 524/555 |
| 4,332,657 | 6/1982 | Makuuchi et al. | 523/300 |
| 4,425,326 | 1/1984 | Giullon et al. | 424/61 |

FOREIGN PATENT DOCUMENTS

| | | |
|---|---|---|
| 2247145 | 9/1972 | Fed. Rep. of Germany . |
| 1133410 | 11/1968 | United Kingdom . |
| 1527555 | 10/1978 | United Kingdom . |
| 2073229 | 10/1981 | United Kingdom . |

*Primary Examiner*—J. R. Brown
*Assistant Examiner*—Wendy B. Davis
*Attorney, Agent, or Firm*—Steele, Gould & Fried

[57] ABSTRACT

The invention relates to nitrocellulose free nail lacquer compositions comprising copolymers of hydrophobic and hydrophilic monomers, in suitable carriers. The nail lacquer compositions may be applied to nails where they form a high gloss, well adhering waterproof film. A process for forming nitrocellulose free nail lacquer compositions is also provided.

9 Claims, No Drawings

NITROCELLULOSE FREE NAIL LACQUER COMPOSITION

This is a continuation-in-part, of application Ser. No. 809,948, filed Dec. 17, 1985 now abandoned which is a continuation of Ser. No. 635,723 filed 7-30-84, now abandoned which is a continuation of Ser. No. 342,397 filed 1-25-82, now abandoned.

BACKGROUND OF THE INVENTION

Conventional nail lacquer compositions rely on nitrocellulose as the primary film former. While nitrocellulose is the film former of choice, it has numerous disadvantages. For example, nitrocellulose discolors with age, is prone to undergo sharp viscosity changes rendering nail lacquer compositions difficult to apply, and it can be difficult to dry to a hard film. Furthermore, car must be taken to insure that nitrocellulose used in formulating nail lacquers is neutral, i.e., acid free, because the presence of free acid could cause damage to fingernails and the cuticle, as well as have a deleterious effect on colorants present in nail lacquers.

Of course, those skilled in the art recognize that nitrocellulose must be produced and handled with great caution and care. The danger of explosion and fire inherent in nitrocellulose production and formulation of compositions containing nitrocellulose is responsible in large measure for the fact that there are very few domestic manufacturers of this product, and only a few domestic formulators of nail lacquers.

The art has frequently sought substitutes for nitrocellulose as a film former for nail lacquers. Attempts to find substitutes for nitrocellulose have not been successful, because, despite its many drawbacks, nitrocellulose provides nail lacquer compositions with an unusual combination of desirable properties such as toughness, durability and solvent release, and it produces waterproof and atmospherically stable films. For examples of such attempts see U.S. Pat. Nos. 3,840,490; 3,864,294; 3,927,203; 3,298,113 and 4,240,450. Typical nitrocellulose containing nail lacquer compositions are described in U.S. Pat. Nos. 4,097,589 and 4,179,304, for example.

There is, therefore, a long felt need in the art for a product which can be substituted for nitrocellulose in the formulation of nail lacquer compositions which will result in finished nail lacquers which are the equivalent of nitrocellulose containing lacquers.

In addition to nitrocellulose film formers, conventional nail lacquer compositions include a resin, plasticizer, solvent and pigments. Plasticizers function to reduce film shrinkage with drying and to give the film flexibility. Solvents provide the lacquer with properties permitting ease of application and affect the rate of drying of the lacquer after application. Pigments or colorants provide the desired color to the nail lacquer.

SUMMARY OF THE INVENTION

An object of this invention is to provide nitrocellulose free nail lacquer compositions.

A further object of this invention is to provide nail lacquer compositions which do not contain nitrocellulose, but which have characteristics and properties which are equivalent to conventional nail lacquer compositions containing nitrocellulose.

A still further object of the invention is to provide nitrocellulose free nail lacquer compositions which, when applied to nails, impart a durable film with high gloss characteristics, flexibility, breathability, and excellent adhesion.

A still further object of the invention is to provide nitrocellulose free nail lacquer compositions which are water insoluble.

DETAILED DESCRIPTION OF THE INVENTION

The present invention relates to nitrocellulose free nail lacquer compositions comprising copolymers of hydrophobic and hydrophilic monomers in a suitable carrier.

According to the present invention there is provided nail lacquer compositions comprising (i) copolymers obtained by polymerizing hydrophobic and hydrophilic monomers, said copolymers being present in said compositions in an amount sufficient to form a film, (ii) a suitable carrier for said copolymers, and (iii) no nitrocellulose. The nail lacquer compositions of this invention impart a high gloss, flexible, breathable, well adhering, waterproof film when applied to nails.

The hydrophobic monomer useful in forming the nail lacquer compositions of this invention comprise esters of $\alpha$-$\beta$ unsaturated carboxylic acids and alcohols of the formula:

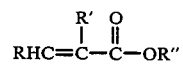

wherein R may be H; $CH_3$; $C_2H_5$; R' may be H; $CH_3$ to $C_4H_9$; and R" may be:

(i) $CH_3$ to $C_4H_9$ straight chain alcohols;
(ii) saturated or unsaturated cyclic alcohols containing up to 20 carbon atoms;
(iii) $C_3H_7$ to $C_{16}H_{37}$ branched alkyl or $C_5H_{11}$ to $C_{22}H_{45}$ straight chain alkyl alcohols; and
(iv) alkoxy or aryloxy alkyl alcohols.

The hydrophobic monomers useful in forming the copolymers comprising the nail lacquer compositions of this invention preferably comprise a delicate and carefully balanced mixture of each of the four classes of esters described above. The hydrophobic monomers may comprise, for example, mixtures formed with from:

(i) about 5 to about 48%, by weight, straight chain alcohols;
(ii) about 5 to about 50%, by weight, saturated or unsaturated cyclic alcohols;
(iii) about 1 to about 25%, by weight, branched alkyl or straight chain higher alkyl alcohols; and
(iv) about 1 to about 30% alkoxy or aryloxy alkyl alcohols.

Especially preferred nail lacquer compositions of this invention include those wherein the hydrophobic monomers comprise mixtures of esters, comprising from:

(i) about 30%, by weight, straight chain alcohols;
(ii) about 40%, by weight, saturated or unsaturated cyclic alcohols;
(iii) about 15%, by weight, branched alkyl or straight chain higher alkyl alcohols; and
(iv) about 10%, by weight, alkoxy or aryloxy alcohols.

The esters formed with the straight chain alcohols defined above which are useful as hydrophobic monomers in forming the nail lacquer compositions of this invention include methyl acrylate, methyl methacrylate, ethyl acrylate, ethyl methacrylate, propyl acrylate, propyl methacrylate, butyl acrylate or butyl methacrylate. Hydrophobic monomers of this type are thought to impart hardness to films provided by the nail lacquer compositions of this invention. Esters formed with saturated or unsaturated cyclic alcohols described above which are useful as hydrophobic monomers for preparing the nail lacquer compositions of this invention include cyclohexyl acrylate, cyclohexyl methacrylate, benzyl acrylate, benzyl methacrylate, isobornyl acrylate, isobornyl methacrylate, adamantyl acrylate, adamantyl methacrylate, furfuryl acrulate and furfuryl methacrylate. Hydrophobic monomers of this type are thought to impart gloss and hardness to films provided by the nail lacquer compositions of this invention. Esters of branched alkyl or straight chain higher alkyl alcohols described above which are useful as hydrophobic monomers for preparing the nail lacquer compositions of this invention include 2-ethylhexyl acrylate, 2-ethylhexyl methacrylate, isobutyl acrylate, isobutyl methacrylate, isooctyl acrylate, isooctyl methacrylate, dodecylacrylate, dodecyl methacrylate, octadodecyl acrylate and octadodecyl methacrylate. Hydrophobic monomers of this type are brought to impart internal plasticization, pliability and breathability to nail lacquer compositions of this invention. Esters of alkoxy or aryloxy alkyl alcohols useful as hydrophobic monomers for preparing the nail lacquer compositions of this invention include methoxyethyl acrylate, methoxyethyl methacrylate, ethoxyethyl acrylate, ethoxyethyl methacrylate, propoxyethyl acrylate, propoxyethyl methacrylate, butoxyethyl acrylate, butoxyethyl methacrylate, phenoxyethyl acrylate, and phenoxyethyl methacrylate. Hydrophobic monomers of this type are thought to impart gloss, flexibility and adhesion to films provided by the nail lacquer compositions of this invention.

While it is preferred that the hydrophobic monomers useful in forming the copolymers be comprised of a mixture of each of the four classes of esters described above, it will be appreciated that the hydrophobic monomer portion of the copolymers may be comprised of a mixture of any two or more of the four classes of esters. When the monomers comprising the hydrophobic portion consist of monomers from less than each of the four classes of esters described above, it is generally preferred that monomers from either of classes (i) or (ii) be present in the hydrophobic monomer portion.

Hydrophilic monomers are copolyermized with the hydrophobic monomers described above in forming the nail lacquer compositions of this invention. "Hydrophilic" monomers in the context of this invention are meant to encompass those monomers which impart dual funtionality to the nail lacquer compositions whereby such compositions will interact with receptor sites of human nails providing for nail lacquer films which demonstrate excellent adhesion, durability, breathability and high gloss. There are numerous hydrophilic monomers useful in the invention. Preferred hydrophilic monomers include (i) N-substituted acrylamides or methacrylamides, (ii) $\alpha$-$\beta$ unsaturated carboxylic acids, and (iii) hydroxyl alkyl acrylates and methacrylates and their homologs. N-substituted acrylamides or methacrylamides useful as hydrophilic monomers in preparing the nail lacquer compositions of this invention include diacetone acrylamide and its homologs as described in U.S. Pat. No. 3,277,056, dimethyl acrylamide, butyl acrylamide, octyl acrylamide, and isobutyl methyl acrylamide. The acrylamide hydrophilic monomers are thought to impart adhesion and breathability to films formed with the nail lacquer compositions of this invention.

The $\alpha$-$\beta$ unsaturated carboxylic acid hydrophilic monomers useful in forming the nail lacquer compositions of this invention include acrylic acid, methacrylic acid, crotonic acid, itaconic acid, maleic acid and fumaric acid. The hydrophilic monomers of this type are thought to impart adhesion to films formed from the nail lacquer compositions of this invention.

The hydroxyalkyl acrylates and methacrylates and their homologs useful in forming the nail lacquer compositions of this invention include hydroxyethyl acrylate and methacrylate, diethylene glycol monoacrylate and monomethacrylate, thriethylene glycol monoacrylate and monomethacrylate, tetraethylene glycol monoacrylate and monomethacrylate, polyethylene glycol monoacrylate and monomethacrylate of molecular weight up to 1000, linear or branched hydroxypropyl acrylate and methacrylate, dipropylene glycol monoacrylate and monomethacrylate, tripropylene glycol monoacrylate and monomethacrylate, tetrapropylene glycol monoacrylate and monomethacrylate, and polypropylene glycol monoacrylate and monomethacrylate of molecular weight up to 1000. Hydrophilic monomers of this type are though to provide improved permeability to films provided by the nail lacquer compositions of the invention.

The hydrophilic monomers useful in forming the nail lacquer compositions of the invention comprise mixtures of from about 50 to about 75%, preferably about 60 to about 65%, by weight, of the acrylamides described above and from about 25 to about 50%, preferably about 35 to about 40%, by weight, of the $\alpha$-$\beta$ unsaturated carboxylic acids described above. Hydroxyalkyl acrylates and methacrylates and their homologs may be included in the nail lacquer compositions of the invention in a ratio of 1:1 with the other hydrophilic monomers described herein.

As stated, the nitrocellulose free nail lacquer compositions of this invention comprise copolymers of the hydrophobic and hydrophilic monomers described hereinabove in a suitable carrier. Preferably, the nail lacquer compositions of this invention are formulated so that the hydrophobic monomers comprise a major portion of the copolymer. For example, typical nail lacquer compositions of this invention are those wherein the copolymer comprises from about 70 to about 95% hydrophobic monomers, and from about 5 to about 30% hydrophilic monomers, said percentages being by weight, based on the weight of the copolymer compositions excluding carrier.

A particularly significant aspect of the invention lies in the fact that the new nail lacquer compositions represent a balance of hydrophobic and hydrophilic characteristics which impart dual functionality to the films obtained on application of the compositions to the nails. In the course of this invention, it has been found that the dual functional nature of the copolymer systems comprising the nail lacquer compositions provides nail lacquer films which have high gloss, flexibility, excellent adhesive properties, breathability, and excellent water resistant properties. It is a particularly significant aspect of this invention that such properties are provided by nail lacquer compositions which do not contain nitrocellulose, on the one hand, but which, on the other, do contain hydrophilic monomers, a component which those skilled in the art would ordinarily expect to be incompatible with nail lacquer films demonstrating excellent water resistant properties.

The nail lacquer compositions of the invention comprise (i) copolymers obtained by polymerizing the hydrophobic and hydrophilic monomers described above, said copolymers being present in said compositions in an amount sufficient to form a film, and (ii) a suitable carrier whereby said nail lacquer compositions do not contain nitrocellulose and yet impart a high gloss, flexible, breathable, well adhering, waterproof film when applied to nails. Nail lacquer compositions comprising from about 10 to about 40%, by weight, based on the weight of the composition of copolymers obtained by polymerizing hydrophobic and hydrophilic monomers in a suitable carrier are useful in forming highly desirable films when applied to the nails. Particularly preferred nail lacquer compositions of the invention are those in which copolymers of hydrophobic and hydrophilic monomers are present in an amount of from about 30 to about 40%, by weight, based on the weight of the composition.

A particularly desirable attribute of the present invention lies in the fact that it is possible to incorporate colorants into the nail lacquer compositions of the invention without significant risk of explosion or fire which is found when colorants are combined with conventional nail lacquers containing nitrocellulose.

Liquid carriers for the nail lacquer compositions of the invention are preferably selected from materials which are solvents for the copolymers. Suitable solvents include ethyl acetate, amyl acetate, butyl acetate, butyl cellosolve acetate, cellosolve acetate, methyl cellosolve acetate, acetone, methyl ethyl ketone, methyl isobutyl ketone, butyl cellosolve, cellosolve, methyl cellosolve, ethyl alcohol, isopropyl alcohol, butyl alcohol, toluene, and xylene. Other solvents may also be used as carriers as will be appreciated by those in the art. Suitable carriers for the nail lacquer compositions comprise any one or a mixture of any of the foregoing solvents in any proportion. A particularly preferred carrier for the nail lacquer compositions of the invention is a 1:1 mixture of butyl acetate and isopropyl alcohol.

When applied to nails, primarily human nails, the nail lacquer compositions of the invention provide films which are the equivalent of conventional nitrocellulose containing nail lacquers. The nail lacquer compositions of the invention are compatible with conventional plasticizers, colorants, suspending agents, viscosity builders, additional film forming resins and fillers. Plasticizers include those well known in the art such as isopropyl alcohol fatty acid esters, $C_8$ alcohol fatty acid esters, organic succinates, organic phthalates, organic adipates, camphor, and castor oil. Colorants include those well known in the art, particularly pigments, and are included in nail lacquer compositions used to impart color to the nails. Such components can be obtained with nail lacquer compositions of the invention by means well known to those skilled in the art to provide colored nail lacquer compositions of any desired hue. Suspending agents are used in nail lacquer compositions containing colorants, and serve to maintain the colorant in suspension in the nail lacquer composition. Useful viscosity builders include tetraethylene glycol dimethacrylate, trimethylol propane trimethacruylate, tetrahydrofurfuryl methacrylate, and allyl methacrylate. Such components are typically incorporated in nail lacquer compositions of the invention in an amount of from about 0.1 to about 0.5%, preferably about 0.25%, by weight, based on the weight of the nail lacquer composition.

Useful additional film forming resins which may be incorporated in the nail lacquer compositions of this invention include aryl sulfanamide/formaldehyde, sucrose acetate isobutyrate, sucrose benzoate and diethylene/dipropylene glycol dibenzoate which may be incorporated in an amount of from about 0% to about 20%, by weight, preferably about 5 to about 10% by weight, based on the weight of the compositions. Whether clear or colored, the nail lacquer compositions of the invention have a high solids content, and thus, provide an eminently acceptable film on nails with a one coat application.

In addition to empirical comparisons of films provided by the nail lacquer compositions of the invention with those provided by conventional nitrocellulose containing nail lacquers, it is possible to compare properties of films provided by the two types of compositions by applying films of the respective nail lacquer compositions to black glass plates or slides, allowing the films to dry at ambient conditions followed by visual, mechanical or instrumental evaluations of the film properties.

The invention also provides a process for production of nitrocellulose free nail lacquer compositions which comprises combining hydrophobic and hydrophilic monomers in a suitable carrier, polymerizing said monomers producing copolymer nail lacquer compositions in which said copolymer is present in an amount sufficient to form a high gloss, flexible, breathable, well adhering, waterproof film when applied to nails.

Generally, the process involves mixing the hydrophobic and hydrophilic monomers in a suitable solvent-carrier selected from those set forth hereinabove, to form a uniform mixture, and inducing polymerization. Polymerization may be induced by conventional initiators such as peroxides and the like, or by irradiation or redox systems. Polymerization usually occurs at temperatures between about 0° to about 120° C., and preferably at the reflux temperature of the solvent carrier.

The time and temperature of polymerization may be varied in accord with techniques well known in the art. Polymerization results in a clear solution in which the copolymer is present in an amount of from about 10% to about 40%, by weight, based on the weight of the composition.

The nail lacquer compositions of this invention offer numerous advantages over conventional, nitrocellulose containing nail lacquer compositions. For example, nitrocellulose is difficult to dissolve. Frequently, aromatic solvents including benzene and toluene are required to dissolve nitrocellulose in conventional nail lacquer formulations. The nail lacquer compositions of this invention do not require use of such potentially toxic solvents and instead, require use of simple solvents such as alcohols. Moreover, pigments and colorants may be incorporated in the nitrocellulose free nail lacquer compositions of the invention without the great fear of fire and explosion inherent when pigments are milled in nitrocellulose base nail lacquer compositions.

The invention is further described by reference to the following examples which are intended to be illustrative of the invention.

EXAMPLE 1

A nail lacquer composition was prepared by mixing the following ingredients in a 3 L, three neck around bottom flask equipped with a stirrer, thermometer and condenser, and heating the mixture at the reflux temperature of the solvent from about 2 to about 24 hours.

| INGREDIENT | AMOUNT (GRAMS) |
| --- | --- |
| Diacetone acrylamide | 46.5 |
| Isobornyl methacrylate | 178.5 |
| Ethyl methacrylate | 150 |
| Phenoxyethyl methacrylate | 55 |
| Methacrylic acid | 30 |
| 2-Ethylhexyl methacrylate | 65 |
| Butyl acetate | 395 |
| Isopropanol | 395 |
| Benzoyl peroxide | 2.85 |

The resulting copolymer was a clear, viscous liquid which when applied to nails provided a high gloss, long lasting film which was the equivalent of conventional nitrocellulose containing nail lacquers.

EXAMPLE 2

Using the equipment and following the procedure of Example 1, the following ingredients were combined and polymerized.

| INGREDIENT | AMOUNT (GRAMS) |
| --- | --- |
| Diacetone acrylamide | 93 |
| Isobornyl methacrylate | 371 |
| Methyl methacrylate | 302 |
| Phenoxyethyl acrylate | 69 |
| 2-Ethylhexyl methacrylate | 174 |
| Methacrylic acid | 47 |
| Tetrahydrofurfuryl methacrylate | 2.5 |
| Butyl acetate | 1455 |
| Benzoyl peroxide | 5.75 |

The resulting copolymer was a clear, viscous liquid which provided a film when applied to nails which was the equivalent of conventional nitrocellulose containing nail lacquers.

EXAMPLE 3

A nail lacquer composition was prepared by mixing the following ingredients in a 0.5 L pressure bottle and heating the mixture at about 90° C. for about 24 hours with constant agitation.

| INGREDIENT | AMOUNT (GRAMS) |
| --- | --- |
| Diacetone acrylamide | 4.25 |
| Dimethyl acrylamide | 4.25 |
| Ethyl methacrylate | 25.5 |
| Cyclohexyl methacrylate | 34 |
| Phenoxyethyl methacrylate | 8.5 |
| Methacrylic acid | 4.25 |
| Tetrahydrofurfuryl methacrylate | 0.2 |
| Butyl acetate | 78.5 |
| Isopropanol | 78.5 |
| Benzoyl peroxide | 2.2 |

The resulting copolymer was a clear, viscous liquid which provided a film when applied to nails which was the equivalent of conventional nitrocellulose containing nail lacquers.

EXAMPLE 4

Using the equipment and following the procedure of Example 3, the following ingredients were combined and polymerized.

| INGREDIENT | AMOUNT (GRAMS) |
| --- | --- |
| Diacetone acrylamide | 4.25 |
| Dimethyl acrylamide | 4.25 |
| Butyl methacrylate | 25.5 |
| Cyclohexyl methacrylate | 34 |
| Phenoxyethyl methacrylate | 8.5 |
| Methacrylic acid | 4.25 |
| Tetrahydrofurfuryl methacrylate | 0.2 |
| Butyl acetate | 78.5 |
| Isopropanol | 78.5 |
| Benzoyl peroxide | 2.2 |

The resulting copolymer was a clear, viscous liquid which provided a film when applied to nails which was the equivalent of conventional nitrocellulose containing nail lacquers.

EXAMPLE 5

Using the equipment and following the procedure of Example 3, the following ingredients were combined and polymerized at a temperature of about 80° C.

| INGREDIENT | AMOUNT (GRAMS) |
| --- | --- |
| Diacetone acrylamide | 8.75 |
| Hydroxyethyl methacrylate | 8.75 |
| Cyclohexyl methacrylate | 36.75 |
| Ethyl methacrylate | 17.50 |
| Isodecyl methacrylate | 8.75 |
| Methacrylic acid | 7 |
| Butyl acetate | 81.25 |
| Ethyl acetate | 81.25 |
| Benzoyl peroxide | 1.75 |

The resulting copolymer was a clear, viscous liquid which provided a film when applied to nails which was the equivalent of conventional nitrocellulose containing nail lacquers.

EXAMPLE 6

Using the equipment and following the procedure of Example 3, the following ingredients were combined and polymerized at a temperature of about 120° C.

| INGREDIENT | AMOUNT (GRAMS) |
| --- | --- |
| N—(iso-butoxymethyl) acrylamide | 8.5 |
| Isobornyl methacrylate | 34.4 |
| Methyl methacrylate | 34.4 |
| Methacrylic acid | 4.25 |
| Tetrahydrofurfuryl methacrylate | 0.17 |
| Butyl acetate | 158 |
| t-Butyl peroctoate | 1.9 ml |

The resulting copolymer was a clear, viscous liquid which provided a film when applied to nails which was the equivalent of conventional nitrocellulose containing nail lacquers.

EXAMPLE 7

Using the equipment and following the procedure of Example 3, the following ingredients were combined and polymerized at a temperature of about 120° C.

| INGREDIENT | AMOUNT (GRAMS) |
| --- | --- |
| Diacetone acrylamide | 4.25 |
| Octyl acrylamide | 5.25 |
| Methyl methacrylate | 34.42 |
| Isobornyl methacrylate | 34.42 |
| Methacrylic acid | 4.25 |
| Tetrahydrofurfuryl methacrylate | 0.17 |
| Butyl acetate | 158 |
| t-Butyl peroctoate | 1.9 ml |

The resulting copolymer was a clear, viscous liquid which provided a film when applied to nails which was the equivalent of conventional nitrocellulose containing nail lacquers.

EXAMPLE 8

Using the equipment and following the procedure of Example 3, the following ingredients were combined and polymerized at a temperature of about 120° C.

| INGREDIENT | AMOUNT (GRAMS) |
| --- | --- |
| Diacetone acrylamide | 8.5 |
| Methyl methacrylate | 34.4 |
| Methoxyethyl methacrylate | 34.4 |
| Methacrylic acid | 4.25 |
| Tetrahydrofurfuryl methacrylate | 0.17 |
| Butyl acetate | 158 |
| t-Butyl peroctoate | 1.9 |

The resulting copolymer was a clear, viscous liquid which provided a film when applied to nails which was the equivalent of conventional nitrocellulose containing lacquers.

EXAMPLE 9

A nail lacquer composition was prepared by combining and mixing 65.5 parts of the base polymer solution of Example 1, 11.5 parts sucrose benzoate, 5 parts castor oil and 18 parts isopropanol until a clear, uniform composition was obtained. The presence of a plasticizer such as castor oil provides improved pliability of the film.

EXAMPLE 10

A nail lacquer composition was prepared by combining and mixing 75 parts base polymer solution of Example 1, 10 parts aryl sulfonamide/formaldehyde (Santolite MHP/Monsanto), and 15 parts isopropanol until a clear, uniform composition was obtained. The composition was the equivalent of nitrocellulose nail lacquer compositions when applied to nails.

EXAMPLE 11

A nail lacquer composition was prepared by combining and mixing 67.5 parts of base polymer solution of Example 1, 11.8 parts of sucrose acetate isobutynate, 18.5 parts of isopropanol, 1 part castor oil and 1 part Timiron MP-1005 (Rona Pearl, Bayonne, N.J.) pigment. Mixing continued until the pigment was uniformly dispersed and the resultant pigmented nail lacquer when applied to nails was the equivalent of conventional nitrocellulose containing nail lacquers.

EXAMPLE 12

A nail lacquer composition was prepared by combining and mixing 50 parts of base polymer solution of Example 1, 5 parts of dipropylene glycol dibenzoate, 1 part isopropyl myristate and 44 parts isopropanol. The resulting copolymer was a clear, viscous liquid which provided a film when applied to nails which was the equivalent of conventional nitrocellulose containing lacquers.

What is claimed is:

1. In an anhydrous waterproof nitrocellulose free nail lacquer composition for human nails containing about 10 to about 40%, by weight, copolymers the improvement comprises copolymers which are the reaction products of about 5 to about 30%, by weight, of diacetone acrylamide and about 70 to about 95%, by weight, of esters of $\alpha, \beta$ unsaturated carboxylic acids and alcohols, said esters formed from a mixture comprising:
   (i) about 5 to about 48%, by weight, of straight chain alcohols,
   (ii) about 5 to about 60%, by weight, of cyclic alcohols,
   (iii) about 1 to about 25%, by weight, of higher alkyl alcohols, and
   (iv) about 1 to about 30%, by weight, of alkoxy or aryloxy alkyl alcohols.

2. In an anhydrous waterproof nitrocellulose free nail lacquer composition for human nails containing about 10 to about 40%, by weight, copolymers, the improvement comprises copolymers which are the reaction products of about 5 to about 30%, by weight, of diacetone acrylamide and about 70 to about 95%, by weight, of esters of $\alpha, \beta$ unsaturated carboxylic acids and alcohols, said esters formed from a mixture comprising
   (i) about 5 to 48%, by weight, of straight chain alcohols, and
   (ii) about 5 to about 60%, by weight, of cyclic alcohols.

3. An anhydrous waterproof nitrocellulose free nail lacquer composition for human nails comprising from about 10 to 40% by weight of copolymers of diacetone acrylamide and hydrophobic monomers, said hydrophobic monomers being a mixture of at least two different esters of $\alpha, \beta$ unsaturated carboxylic acids, said esters being selected from the group consisting of:
   (i) methyl acrylate, methyl methacrylate, ethyl acrylate, ethyl methacrylate, propyl acrylate, propyl methacrylate, butyl acrylate, butyl methacrylate,
   (ii) cyclohexyl acrylate, cyclohexyl methacrylate, benzyl acrylate, benzyl methacrylate, isobornyl acrylate, isobornyl methacrylate, adamantyl acrylate, adamantyl methacrylate, furfuryl acrylate, furfuryl methacrylate,
   (iii) 2-ethylhexyl acrylate, 2-ethylhexyl methacrylate, isobutyl acrylate, isobutyl methacrylate, isooctyl acrylate, isooctyl mehtacrylate, dodecylacrylate, dodecyl methacrylate, octadodecyl acrylate, octadodecyl methacrylate, isodecyl acrylate, isodecyl methacrylate,
   (iv) methoxyethyl acrylate, methoxyethyl methacrylate, ethoxyethyl acrylate, ethoxyethyl methacrylate, propoxyethyl acrylate, propoxyethyl methacrylate, butoxyethyl acrylate, butoxyethyl methacrylate, phenoxyethyl acrylate, and phenoxyethyl methacrylate;
   said copolymers comprising from about 70% to about 95% by weight of said hydrophobic monomers and from about 5 to about 30% by weight of diacetone acrylamide, said percentages being by weight, and a nitrocellulose free carrier.

4. The nail lacquer composition of claim 2 including a solvent selected from the group consisting of ethyl acetate, amyl acetate, butyl acetate, butyl cellosolve acetate, cellosolve acetate, methul cellosolve acetate, acetone, methy ethyl ketone, methyl isobutyl ketone, butyl cellosolve, cellosolve, methyl cellosolve, ethyl alcohol, ispropyl alcohol, butyl alcohol, toluene, and xylene.

5. The nail lacquer composition of claim 4 wherein said solvent is a 1:1 mixture of butyl acetate and isopropyl alcohol.

6. The nail lacquer composition of claim 2 further comprising colorants, suspending agents and fillers.

7. The nail lacquer composition of claim 2 further comprising at least one of an additional film forming resin and a plasticizer.

8. The nail lacquer composition of claim 7 including viscosity builders selected from the group consisting of ethylene glycol dimethacrylate, tetraethylene glycol dimethacrylate, trimethylol propane trimethacrylate, tetrahydrofurfuryl methacrylate and allyl methacrylate in an amount of from about 0.1 to about 0.5%, by weight, based on the weight of said composition.

9. In an anhydrous waterproof nitrocellulose free nail lacquer composition for human nails containing copolymers and which is free of nitrocellulose, the improvement which comprises the copolymers being formed by the reaction of the following:

| INGREDIENT | AMOUNT (GRAMS) |
| --- | --- |
| Diacetone acrylamide | 46.5 |
| Isobornyl methacrylate | 178.5 |
| Ethyl methacrylate | 150 |
| Phenoxyethyl methacrylate | 55 |
| Methacrylic acid | 30 |
| 2-Ethylhexyl methacrylate | 65 |
| Butyl acetate | 395 |
| Isopropanol | 395 |
| Benzoyl peroxide | 2.85 |

* * * * *

UNITED STATES PATENT AND TRADEMARK OFFICE
CERTIFICATE OF CORRECTION

PATENT NO. : 4,762,703

DATED : August 9, 1988

INVENTOR(S) : Eric S. Abrutyn

It is certified that error appears in the above-identified patent and that said Letters Patent is hereby corrected as shown below:

```
Col. 1, line 18, "car" should be --care--.
Col. 2, line 47, "50%" should be --60%--.
Col. 3, line 22, "brought" should be --thought--.
Col. 4, line 25 "hought" should be --thought--.
Col. 5, line 57 "obtained" should be --combined--.
Col. 7, line 3, "around" should be --round--.
```

Signed and Sealed this

Thirty-first Day of January, 1989

Attest:

DONALD J. QUIGG

*Attesting Officer*  *Commissioner of Patents and Trademarks*